US012612417B2

(12) United States Patent
Arsenjans

(10) Patent No.: US 12,612,417 B2
(45) Date of Patent: Apr. 28, 2026

(54) DEUTERATED ANALOGUES OF SELENOPHENOCHROMENES, SYNTHESIS THEREOF, AND METHODS OF USING SAME AGENTS

(71) Applicant: Latvian Institute of Organic Synthesis, Riga (LV)

(72) Inventor: Pavels Arsenjans, Riga (LV)

(73) Assignee: Latvian Institute of Organic Synthesis, Riga (LV)

( * ) Notice: Subject to any disclaimer, the term of this patent is extended or adjusted under 35 U.S.C. 154(b) by 587 days.

(21) Appl. No.: 17/785,205

(22) PCT Filed: Jul. 21, 2020

(86) PCT No.: PCT/IB2020/056817

§ 371 (c)(1),
(2) Date: Jun. 14, 2022

(87) PCT Pub. No.: WO2021/123928

PCT Pub. Date: Jun. 24, 2021

(65) Prior Publication Data

US 2023/0002411 A1 Jan. 5, 2023

(30) Foreign Application Priority Data

Dec. 20, 2019 (LV) ........................................ P-19-75

(51) Int. Cl.

| | |
|---|---|
| ***C07D 517/04*** | (2006.01) |
| ***A61K 31/496*** | (2006.01) |
| ***A61K 45/06*** | (2006.01) |
| ***A61P 35/00*** | (2006.01) |

(52) U.S. Cl.

CPC .......... *C07D 517/04* (2013.01); *A61K 31/496* (2013.01); *A61K 45/06* (2013.01); *A61P 35/00* (2018.01); *C07B 2200/05* (2013.01)

(58) Field of Classification Search

CPC ........ A61P 35/00; A61K 31/496; A61K 45/06

See application file for complete search history.

(56) References Cited

U.S. PATENT DOCUMENTS

2019/0298758 A1 10/2019 Arsenjans et al.

FOREIGN PATENT DOCUMENTS

| | | | |
|---|---|---|---|
| AU | 2018234985 | 10/2019 | |
| EP | 3492470 | 6/2019 | |
| WO | WO 2012158885 | 11/2012 | |
| WO | WO 2018015788 | 1/2018 | |
| WO | WO-2018015788 A1 * | 1/2018 | ........... C07D 517/04 |
| WO | WO 2018167203 | 9/2018 | |
| WO | WO 2019183403 | 9/2019 | |

OTHER PUBLICATIONS

Tung et al. Deuterium Medicinal Chemistry: A New Approach to Drug Discovery and Development, MEDCHEM News, May 2014, pp. 8-22. (Year: 2014).*

Avanir.com [online], "Avanir Pharmaceuticals, Inc. Reports Phase 3 Data Evaluating Investigational AVP-786 for the Treatment of Moderate-to-Severe Agitation in Patients with Alzheimer's Dementia," Mar. 2019, retrieved Jun. 13, 2022, retrieved from URL<https://www.avanir.com/press/avanir-pharmaceuticals-inc-reports-phase-3-data-evaluating-investigational-avp-786-treatment>, 7 pages.

ClinicalTrials.gov [online], "First-in-Human Study of the Safety, Tolerability, and Pharmacokinetic/Pharmacodynamic Profile of VX-984 in Combination With Chemotherapy," NCT02644278, last updated Sep. 9, 2019, retrieved on Jun. 13, 2022, retrieved from URL<https://clinicaltrials.gov/ct2/show/study/NCT02644278>, 34 pages.

International Search Report and Written Opinion in International Appln. No. PCT/IB2020/056817, dated Oct. 16, 2020, 8 pages.

Khan et al., "VX-984 is a selective inhibitor of non-homologous end joining, with possible preferential activity in transformed cells," Oncotarget, May 2018, 9(40):25833-41.

Schmidt, "First deuterated drug approved," Nat. Biotechnol., Jun. 2017, 35(6):493-94.

Siegel et al., "Cancer statistics, 2019," CA Cancer J. Clin., Jan. 2019, 69(1):7-34.

Fukuto et al., "Determination of the mechanism of demethylenation of (methylenedioxy) phenyl compounds by cytochrome P450 using deuterium isotope effects," Journal of Medicinal Chemistry, Sep. 1991, 34(9):2871-6.

* cited by examiner

*Primary Examiner* — Sarah Pihonak
*Assistant Examiner* — Mikhail O'Donnel Robinson
(74) *Attorney, Agent, or Firm* — Fish & Richardson P.C.

(57) ABSTRACT

The present invention relates to a novel cancer curing deuterated selenopheno [h] chromene derivatives, as well as methods of their manufacturing and use in different pharmaceutical compositions for the treatment of cancer by administration of such substances.

10 Claims, 1 Drawing Sheet

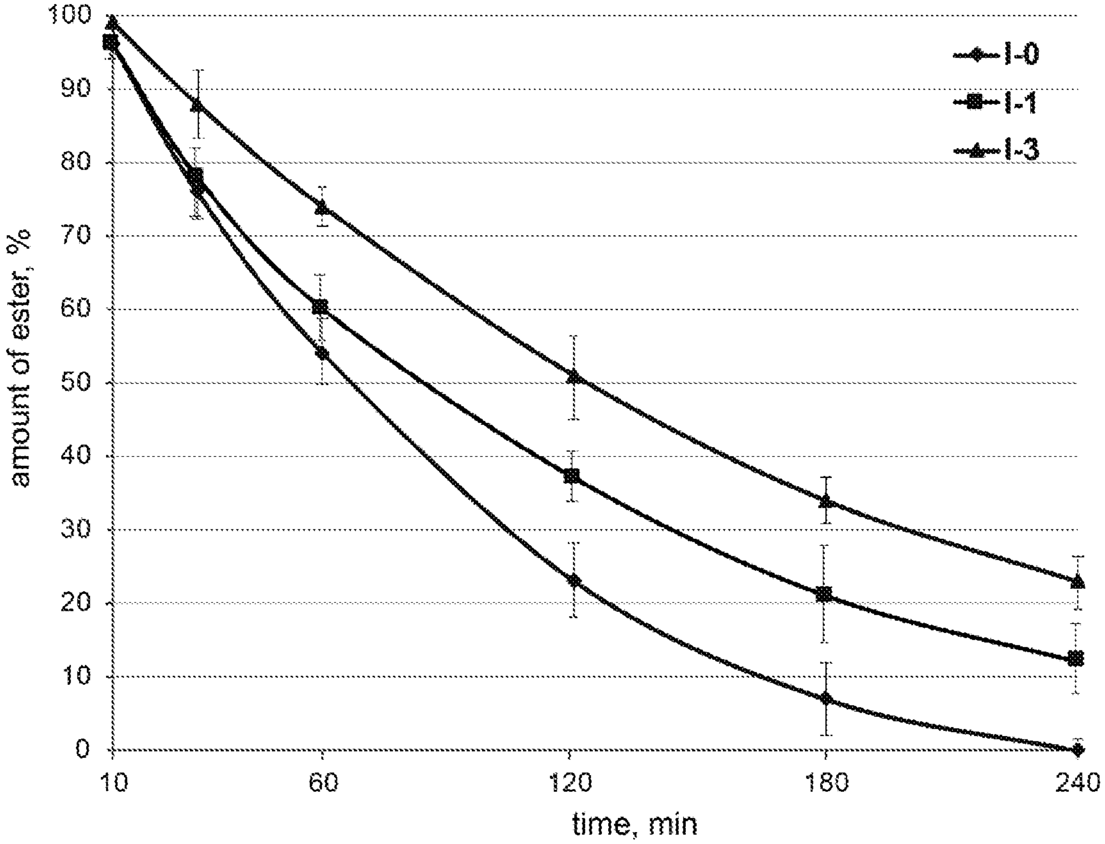
100
90
80
70
60
50
40
30
20
10
0
amount of ester, %
10
60
120
180
240
time, min
I-0
I-1
I-3

DEUTERATED ANALOGUES OF SELENOPHENOCHROMENES, SYNTHESIS THEREOF, AND METHODS OF USING SAME AGENTS

CROSS REFERENCE TO RELATED APPLICATIONS

This application is a U.S. national phase filing under 35 U.S.C. § 371 of International Application No. PCT/IB2020/056817, filed Jul. 21, 2020, which claims priority to Latvian Application No. P-19-75, filed Dec. 20, 2019. The International Application was published in English on Jun. 24, 2021 as WO 2021/123928 under PCT Article 21(2). The contents of the prior applications are incorporated herein by reference in their entirety.

FIELD OF THE INVENTION

Embodiments herein relate to the field of chemistry and biochemistry, and, more specifically, to anti-cancer compounds, synthesis thereof, and methods of using same. The present invention discloses novel deuterated 2H-selenopheno[3,2-h]chromene derivatives, a process of the manufacture and the use of the disclosed compounds for treatment of cancer.

BACKGROUND OF THE INVENTION

Oncologic diseases are among the leading causes of death in economically developed countries,[1] and in the recent years the number of deaths due to malignancies has nearly doubled. More than 7 million people diagnosed with various forms of cancer die every year, according to the data provided by the International Health Organization.

The introduction of deuterium in drugs and active drug candidates is a modern technique which is used in purpose to increase lipophilicity and functional groups stability against hydrolysis during metabolism. Although first deuterated compound was patented more than 40 years ago, FDA approved first deuterium containing drug named Deutetrabenazine[2] in 2017. In last decade various deuterated compounds were patented.[3-5] Few of them are in clinical trials, such as AVP-786 (combination of deudextromethorphan hydrobromide and quinidine sulfate) for the treatment of moderate-to-severe agitation in patients with Alzheimer's dementia[6]; Deutivacaftor (N-[2-tert-butyl-4-[1,1,1,3,3,3-hexadeuterio-2-(trideuteriomethyl)propan-2-yl]-5-hydroxyphenyl]-4-oxo-1H-quinoline-3-carboxamide) for the treatment of cystic fibrosis,[7] VX-984[8,9] for the treatment of solid tumors.

Recently we have surprisingly discovered that certain novel 2H-selenopheno[3,2-h]chromene derivatives with low or medium cytotoxicity on cancer cell lines unexpectedly have excellent antimetastatic activity in vivo against various cancers.[10] However, these compounds exhibit modest ability to in vivo suppress primary tumors growth.

THE PRESENT INVENTION

We have surprisingly discovered that certain novel deuterated 2H-selenopheno[3,2-h]chromene derivatives are more stable during in vitro experiments which resulted in higher cytotoxicity against cancer cells. These novel compounds can be used for manufacturing of a various pharmaceutical composition, wherein they are present together with one or more pharmaceutically acceptable diluents, carriers, or excipients.

OBJECTS OF THE INVENTION

An object of the present invention are selenium-containing novel compounds bearing deuterium with anticancer properties, useful for treatment of primary cancers, methods for manufacturing of disclosed compounds and the treatment of various cancers by administration of such substances.

SUMMARY OF THE INVENTION

We disclosed compounds selected from those of Formula I

I

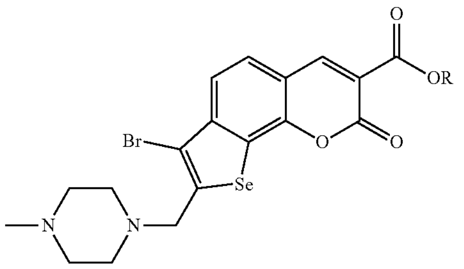

wherein

R represents $C_1$-$C_7$ alkyl group containing deuterium.

As used herein, the term "alkyl" refers to a straight or branched hydrocarbon chain, containing the indicated number of carbon atoms. For example, $C_1$-$C_6$ alkyl indicates that the alkyl group may have from 1 to 6 (inclusive) carbon atoms.

Specific compounds of Formula I within the present invention include but are not limited to:

Methyl-d3 7-bromo-8-((4-methylpiperazin-1-yl)methyl)-2-oxo-2H-selenopheno[3,2-h]chromene-3-carboxylate;

Ethyl-d5 7-bromo-8-((4-methylpiperazin-1-yl)methyl)-2-oxo-2H-selenopheno[3,2-h]chromene-3-carboxylate;

Butyl-d9 7-bromo-8-((4-methylpiperazin-1-yl)methyl)-2-oxo-2H-selenopheno[3,2-h]chromene-3-carboxylate.

BRIEF DESCRIPTION OF DRAWINGS

FIG. 1 depicts the stability of deuterated selenopheno [A] chromenes I-1-I-3 compared with non-deuterated analogue methyl 7-bromo-8- ((4-methylpiperazin-1-yl) methyl) -2-oxo-2H-selenopheno [3,2-h] chromene-3-carboxylate dihydrochloride (1-0) based on in vitro testing using lysate of human hepatoma cells HepG2.

DETAILED DESCRIPTION OF THE INVENTION

Searching for anticancer compounds with improved stability and anticancer activity we unexpectedly discovered that deuterated 2H-selenopheno[3,2-h]chromene derivatives of Formula I exhibit higher stability and cytotoxic effect against cancer cells compared with non-deuterated analogue.

Pharmaceutical compositions in accordance with embodiments of the disclosure may be prepared by combining the disclosed compounds with a solid or liquid pharmaceutically acceptable carrier and, optionally, with pharmaceutically acceptable adjuvants and excipients employing standard and conventional techniques. Solid form compositions include powders, tablets, dispersible granules, capsules, cachets and suppositories. A solid carrier may be at least one substance that may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds disclosed herein dissolved in water and water-propylene glycol systems, optionally containing suitable conventional coloring agents, flavoring agents, stabilizers, and/or thickening agents.

In an embodiment, a pharmaceutical composition may be provided employing conventional techniques in unit dosage form containing effective or appropriate amounts of one or more active component. In embodiments, the quantity of active component (compound) in a pharmaceutical composition and unit dosage form thereof may be varied or adjusted widely depending upon the particular application, the potency of the particular compound and the desired concentration. In an embodiment, the quantity of active component may range from 0.5% to 90% by weight of the composition.

In embodiments, in therapeutic use for treating, ameliorating, preventing, or combating cancer in animals, the compounds or pharmaceutical compositions thereof may be administered orally, parenterally, topically, and/or by inhalation at a dosage to obtain and maintain a concentration or blood-level of active component in the animal undergoing treatment that is therapeutically effective.

In an embodiment, such a therapeutically effective amount of dosage of active component may be in the range of about 0.1 to about 100 mg/kg, more preferably about 3.0 to about 50 mg/kg, of body weight/day. It is to be understood that the dosages may vary depending upon the requirements of the patient, the severity, type, stage, grade, or location of the cancer being treated, and the particular compound being used.

Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose also may be divided into multiple doses for administration, for instance, two to four times per day.

Scheme 1 describes the preparation of compounds of Formula I of the present invention. All of the final compounds of the present invention can be prepared by procedures described in these charts or by procedures analogous thereto, which procedures would be well known to one of ordinary skill in organic chemistry. All of the variables used in the scheme are as defined below or as in the claims.

General Procedure of Compounds Preparation of Formula 1 (Scheme 1)

Scheme 1. General procedure toward compounds of Formula I.

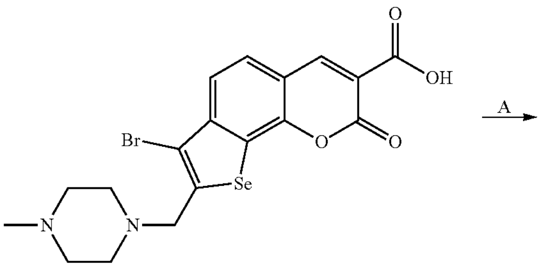

1

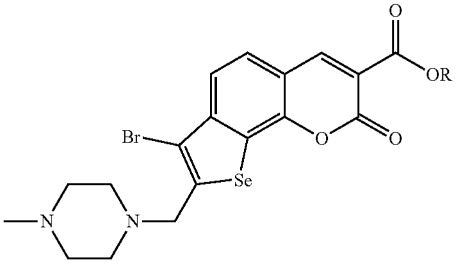

I-1 - I-3

Reaction conditions: A: deuterated alcohol, HOBt, N-methylmorpholine, EDC HCl, DMF.

EXAMPLES

Preparation of the disclosed compounds of the present invention is described in the following examples, which are intended as an illustration of and not a limitation upon the scope of the invention.

Hereinafter, "DMF" is defined as N,N-dimethylformamide, "DMSO" as dimethyl sulfoxide, "HCl" as hydrochloric acid, "HOBt" as hydroxybenzotriazole, "EDC HCl" as 1-ethyl-3-(3-dimethylaminopropyl)carbodiimide hydrochloride "DCM" as dichloromethane, "rt" as room temperature.

General Method for Preparation of Deuterated selenopheno[3,2-h]chromenes (I)

A round bottom flask (100 mL), equipped with a magnetic stirrer and septum, was charged with 7-bromo-8-((4-methylpiperazin-1-yl)methyl)-2-oxo-2H-selenopheno[3,2-h]chromene-3-carboxylic acid dihydrochloride (1, 350 mg, 0.63 mmol), hydroxybenzotriazole (96 mg, 0.63 mmol) and dry DMF (15 mL). Subsequently, after the addition of N-methylmorpholine (134 μL, 1.25 mmol) and appropriated deuterated alcohol (2.51 mmol), 1-ethyl-3-(3-dimethylaminopropyl)carbodiimide hydrochloride (300 mg, 1.57 mmol) was added in one portion. Reaction mixture was stirred overnight, then DMF was evaporated under reduced pressure. Crude residue was purified by flash chromatography on silica gel using DCM/MeOH mixture as eluent. After being purified I-1 was dissolved in DCM and converted to its hydrochloride salt by adding 1M HCl solution in diethyl ether. Products I-2 and I-3 were converted to HCl salts before purification.

Example 1

Methyl-d3 7-bromo-8-((4-methylpiperazin-1-yl)methyl)-2-oxo-2H-selenopheno[3,2-h]chromene-3-carboxylate dihydrochloride (I-1)

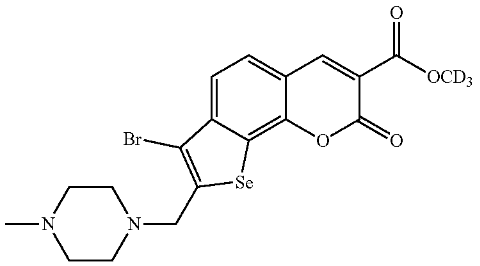

Yield, 69%. M.p.>200° C.

$^{1}$H NMR (400 MHz, Chloroform-d) δ 8.66 (s, 1H), 7.69 (d, 1H), 7.56 (d, 1H), 3.84 (s, 2H), 2.87-2.39 (m, 8H), 2.34 (s, 3H). $^{13}$C NMR (101 MHz, $CDCl_3$) δ 163.9, 156.4, 153.7, 152.8, 150.0, 146.7, 126.1, 125.7, 121.1, 116.4, 113.2, 105.6, 58.8, 55.2, 53.7, 46.0. $^{77}$Se NMR (76 MHz, $CDCl_3$) δ 574.6. HRMS (ESI) calcd for $C_{19}H_{16}D_3BrN_2O_4Se$ $[M+H]^+$ 501.9954, found 501.9965.

Example 2

Ethyl-d5 7-bromo-8-((4-methylpiperazin-1-yl)methyl)-2-oxo-2H-selenopheno[3,2-h]chromene-3-carboxylate dihydrochloride (I-2)

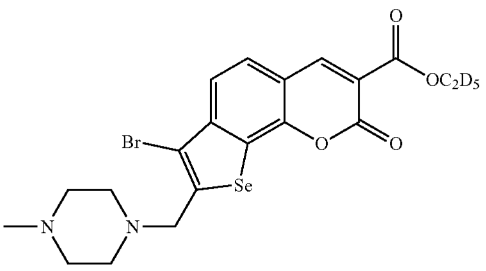

Yield, 92%. M.p.>200° C.

$^{1}$H NMR (400 MHz, Chloroform-d) δ 8.57 (s, 1H), 7.61 (d, 1H), 7.50 (d, 1H), 3.83 (s, 2H), 2.97-2.46 (m, 8H), 2.42 (s, 3H). $^{13}$C NMR (101 MHz, $CDCl_3$) δ 163.0, 156.2, 152.9, 152.5, 149.3, 146.4, 126.0, 125.5, 120.9, 116.6, 113.2, 105.8, 77.5, 58.6, 54.9, 53.0, 45.5. $^{77}$Se NMR (76 MHz, $CDCl_3$) δ 572.8. HRMS (ESI) calcd for $C_{20}H_{16}D_5BrN_2O_4Se$ $[M+H]^+$ 518.0237, found 518.0250.

Example 3

Butyl-d9 7-bromo-8-((4-methylpiperazin-1-yl)methyl)-2-oxo-2H-selenopheno[3,2-h]chromene-3-carboxylate dihydrochloride (I-3)

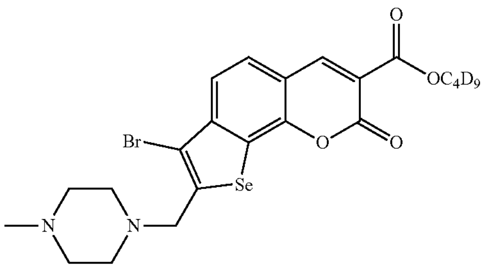

Yield, 80%. M.p.>200° C.

$^{1}$H NMR (400 MHz, Chloroform-d) δ 8.60 (s, 1H), 7.69 (d, 1H), 7.57 (d, 1H), 3.84 (s, 2H), 2.87-2.38 (m, 8H), 2.33 (s, 3H). $^{13}$C NMR (101 MHz, $CDCl_3$) δ 163.2, 156.2, 153.5, 152.7, 149.3, 146.5, 125.9, 125.7, 120.9, 116.8, 113.1, 105.5, 58.8, 55.2, 53.7, 46.0. $^{77}$Se NMR (76 MHz, $CDCl_3$) δ 574.2. HRMS (ESI) calcd for $C_{22}H_{16}D_9BrN_2O_4Se$ $[M+H]^+$ 550.0801, found 550.0808.

Metabolic Stability In Vitro

Assay: the human hepatoma cells HepG2 (ATCC HB-8065) were grown in Eagle's Minimum Essential Medium supplemented with 10% fetal calf serum. The cells were harvested at 80% confluence. The hepatocytes were scraped, two time washed in Hank's Balanced Salt Solution (HBSS) buffer pH-7.4 and suspended in homogenization buffer composed of 10 mM Tris-HCl, 10 mM KCl, 0.15 mM $MgCl_2$ pH 6.7. The cells were homogenized on ice by homogenizer LabGEN7 (Cole Palmer) at 5000 rpm 15 sec. Homogenized cells in HBSS with compound (protein concentration is 95 μg/ml) incubate 37° C. After 10, 30, 60, 120, 180, and 240 min collect 1 ml sample and add 0.1 ml 40% TCA, then centrifugation at 1200 g for 10 min. Supernatant collected and analyzed.

Results: The stability of deuterated selenopheno[h]chromenes I-1-I-3 compared with non-deuterated analogue methyl 7-bromo-8-((4-methylpiperazin-1-yl)methyl)-2-oxo-2H-selenopheno[3,2-h]chromene-3-carboxylate dihydrochloride (I-0) was tested in vitro using lysate of human hepatoma cells HepG2. The results are presented in FIG. 1 (x-axis—minutes of incubation, y-axis—percent of remained ester). Surprisingly, I-3 showed the highest stability to hydrolysis, 24% of deuterated butyl ester remained after 240 minutes of incubation. Notably, I-0 almost completely was hydrolyzed.

Anticancer activity of deuterated selenopheno[h] chromenes was tested in vitro using cytotoxicity assay. Thus, monolayer tumor cell lines MDA-MB-435s (human melanoma), MCF-7 (human breast adenocarcinoma, estrogen-positive), MES-SA (human uterus sarcoma), HT-1080 (human fibrosarcoma), A549 (human lung carcinoma), GM08402 (human fibroblast, apparently healthy), 3T3 (mouse embryo fibroblasts), H9C2 (rat cardiomyocytes) were cultured in standard medium DMEM (Dulbecco's modified Eagle's medium) ("Sigma") supplemented with 10% heat-inactivated fetal bovine serum ("Sigma"). The cell viability was assessed by addition of 3-(4,5-dimethylthiazol-2-yl)-2,5-diphenyltetrazolinium bromide (MTT). Briefly, cells were seeded (2–6×$10^4$ cells/ml) in 96-well plates and allowed to attach for 24 h.

Tested compound solutions were prepared and serially diluted to obtain appropriate concentrations. Cells were treated with different concentrations (0.032-100 μM) and incubated for 48 h at 37° C., 5% $CO_2$ Then the culture medium was removed and medium containing 0.2 mg/ml MTT was added. After 3 h (37° C., 5% $CO_2$), the MTT-containing medium was removed, and 200 μl of dimethyl sulfoxide (DMSO) was immediately added to each sample. The absorbance was assessed at 540 nm on a Tecan multiplate reader Infinite 1000 (Austria). The half-maximal inhibitory concentration ($IC_{50}$) of each compound was calculated using Graph Pad Prism® 3.0.

The results of cell culture-based studies are summarized in Table 1. In general, tested compounds showed medium or low cytotoxicity against malignant tumor cells. However, the introduction of deuterated substituent led to significant increase in cytotoxic effect on triple negative breast carcinoma (MDA-MB-231), sarcoma (MES-SA), fibrosarcoma (HT-1080) and lung carcinoma cell lines (A549) $IC_{50}$ increased up to 29 μM. This unexpected discovery together with increase in stability of compounds I-1-I-3 towards cancer cells makes these compounds very promising as anticancer medicines.

TABLE 1

In vitro cytotoxicity of deuterated selenopheno[h]chromenes on monolayer tumor cell lines.

| | Cytotoxicity $IC_{50}$, μM | | | | | | | |
|---|---|---|---|---|---|---|---|---|
| Nr. | MDA-MB-231 | MCF-7 | MES-SA | HT-1080 | A549 | GM08402 | 3T3 | H9C2 |
| I-0 | 95 ± 4 | 54 ± 6 | 56 ± 1 | 58 ± 5 | >100 | 77 ± 16 | 100 ± 5 | 92 ± 12 |
| I-1 | 84 ± 13 | 82 ± 5 | 40 ± 7 | 70 ± 6 | 105 ± 7 | 89 ± 16 | 66 ± 11 | 82 ± 14 |
| I-2 | 90 ± 15 | 46 ± 4 | 56 ± 15 | 59 ± 6 | >100 | 94 ± 8 | 64 ± 9 | 73 ± 4 |
| I-3 | 35 ± 8 | 70 ± 3 | 29 ± 3 | 31 ± 3 | 40 ± 13 | 62 ± 3 | 34 ± 7 | 30 ± 4 |

REFERENCES

1. R. L. Siegel, K. D. Miller, A. Jemal, Cancer statistics, 2019. CA Cancer J Clin. 2019, 69(1): 7-34.
2. C. Charles Schmidt, First deuterated drug approved. Nature Biotechnol, 2017, 35, 493-494.
3. A. M. G. Bunt, Deuterated analogs of elacridar. WO2019183403 (A1).
4. K. G. Pike, B. C. Barlaam, Deuterated imidazo(4,5-c) quinolin-2-one compounds and their use in treating cancer. AU2018234985 (A1).
5. A. J. Morgan, Deuterated palbociclib with improved metabolic stability. EP3492470 (A1).
6. www.avanir.com/press/avanir-pharmaceuticals-inc-reports-phase-3-data-evaluating-investigational-avp-786-treatment.
7. A. J. Morgan, Deuterated derivatives of ivacaftor. WO2012158885 (A1).
8. A. J. Khan, S. M. Misenko, A. Thandoni, D. Schiff, S. R. Jhawar, S. F. Bunting, B. G. Haffty, VX-984 is a selective inhibitor of non-homologous end joining, with possible preferential activity in transformed cells. Oncotarget. 2018; 9: 25833-25841.
9. clinicaltrials.gov/ct2/ show/NCT02644278.
10. P. Arsenjans, J. Vasiljeva, I. Domracheva, I. Shestakova, I. Kalvins, Antimetastatic 2H-Selenopheno[3,2-h] chromenes, Synthesis Thereof, and Methods of Using Same Agents. US2019298758 (A1).

The invention claimed is:

1. A compound of formula (I), wherein the compound of formula (I) is:

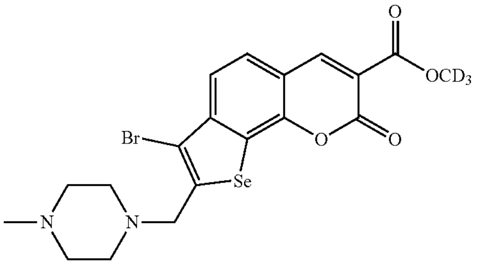

or

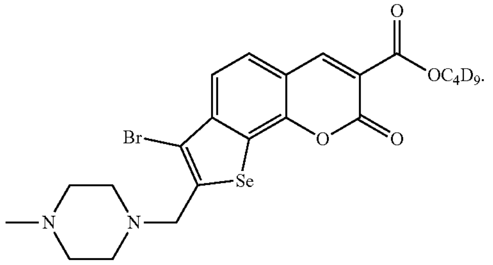

2. The compound according to claim 1, wherein the compound has the structure:

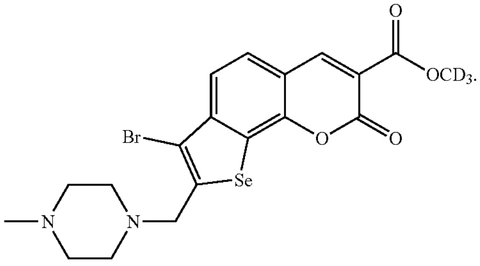

3. The compound according to claim 1, wherein the compound has the structure:

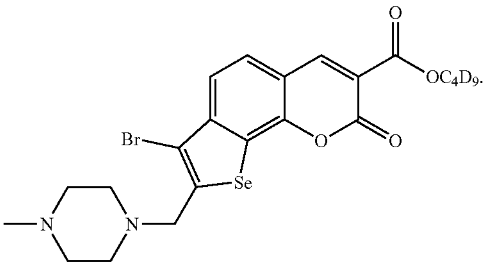

4. A pharmaceutical composition comprising the compound according to claim 1 and a pharmaceutically acceptable carrier.

5. The pharmaceutical composition according to claim 4, wherein the composition is a mono-phasic pharmaceutical composition suitable for parenteral or oral administration consisting essentially of a therapeutically effective amount of the compound of formula I, and a pharmaceutically acceptable carrier.

6. A method of treating cancer, comprising administering a therapeutically effective amount of the compound of claim 1 to a patient in need thereof.

7. The method of claim 6, wherein the cancer is breast, sarcoma, fibrosarcoma, or lung cancer.

8. The method of claim 6, wherein the compound is administered in conjunction with one or more chemotherapeutic agents, surgery, chemotherapy, radiation, immunotherapy, or combinations thereof.

9. The method of claim 6, wherein the compound is

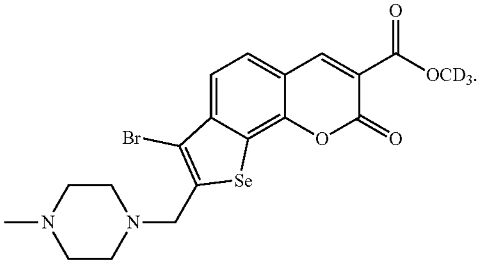

10. The method of claim 6, wherein the compound is

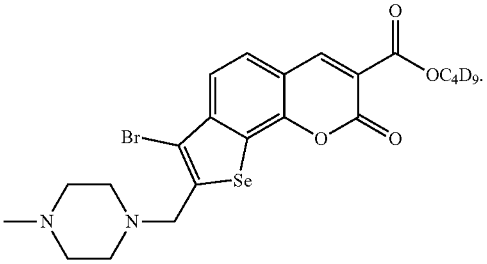

* * * * *